(12) United States Patent
Kawata et al.

(10) Patent No.: US 8,372,611 B2
(45) Date of Patent: Feb. 12, 2013

(54) METHOD FOR PRODUCING POLYHYDROXYALKANOATE (PHAS) USING HALOBACTERIUM AND HALOBACTERIUM

(75) Inventors: Yoshikazu Kawata, Ikeda (JP); Seiichi Aiba, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 121 days.

(21) Appl. No.: 12/674,102

(22) PCT Filed: Sep. 25, 2008

(86) PCT No.: PCT/JP2008/067340
§ 371 (c)(1),
(2), (4) Date: Feb. 18, 2010

(87) PCT Pub. No.: WO2009/041531
PCT Pub. Date: Apr. 2, 2009

(65) Prior Publication Data
US 2011/0104767 A1    May 5, 2011

(30) Foreign Application Priority Data

Sep. 26, 2007   (JP) .................................. 2007-248651

(51) Int. Cl.
*C12P 7/62*    (2006.01)
(52) U.S. Cl. ...................... 435/135; 435/243; 435/252.1
(58) Field of Classification Search .......................... None
See application file for complete search history.

(56) References Cited

FOREIGN PATENT DOCUMENTS
JP          07-303490 A      11/1995

OTHER PUBLICATIONS

ATCC: Catalog Search, Product Details, ATCC 700597.*
Kanekar et al., Proceedings of Taal2007: The 12th World Lake Conference: pp. 1765-1774, 2008.*
Joshi et al., Microbial Ecology (2008), vol. 55, pp. 163-172, published online Jul. 1, 2007.*
Ostle et al., *Applied and Environmental Microbiology*, 44(1): 238-241 (Jul. 1982).
Lillo et al., *Applied and Environmental Microbiology*, 56(8): 2517-2521 (Aug. 1990).
Mata et al., *System. Appl. Microbiol.*, 25: 360-375 (2002).
Quillaguaman et al., *Enzyme and Microbial Technology*, 38: 148-154 (2006).
Quillaguaman et al., *Cellular Origin and Life in Extreme Habitats and Astrobiology*, 9: 357-367 (2005).
Quillaguaman et al., *Journal of Applied Microbiology*, 99(1): 151-157 (2005).
Quillaguaman et al., *Appl. Microbiol. Biotechnol.*, 74(5): 981-986 (2007).
Romano et al., *J. Gen. Appl. Microbiol.*, 52: 339-348 (2006).
Simon-Colin et al., *Journal of Applied Microbiology*, 104: 1425-1432 (May 2008).
Kawata, Yoshikazu, "Bio plastic PHA Production Using Biodiesel Waste Glycerol by *Halomonas* sp. KM-1 Strain," $7^{th}$ *Biomass Asia Workshop*, Jakarta, Indonesia (Nov. 29-Dec. 1, 2010).
Kawata et al., *Biosci. Biotechnol. Biochem.*, 74(1): 175-177 (2010).
European Patent Office, Supplementary European Search Report in European Application No. 08 83 2989 (Jun. 11, 2012).
Japanese Patent Office, International Search Report in International Patent Application PCT/JP2008/067340 (Nov. 4, 2008).
Kawata et al., *Journal of Bioscience and Bioengineering*, 113(4): 456-460 (2012).

* cited by examiner

*Primary Examiner* — Allison Ford
*Assistant Examiner* — Yvonne Pyla
(74) *Attorney, Agent, or Firm* — Leydig, Voit & Mayer, Ltd.

(57) ABSTRACT

Disclosed are a method for producing polyhydroxyalkanoates (PHAs) using a halobacterium belonging to the genus *Halomonas*, wherein the halobacterium can grow in a medium consisting of an inorganic salt and a single organic carbon source and having a pH of 8.8 to 11, and produce PHAs in an amount of 20 wt. % or more based on the dry cell weight, and the halobacterium is cultured in an alkaline medium containing an inorganic salt and one or more organic carbon sources to produce PHAs in an amount of 20 wt. % or more based on the dry cell weight; and the halobacterium belonging to the genus *Halomonas*, which can grow in a medium consisting an inorganic salt and a single organic carbon source and having a pH of 8.8 to 11, and produce PHAs in an amount of 20 wt. % or more based on the dry cell weight.

6 Claims, 6 Drawing Sheets

METHOD FOR PRODUCING POLYHYDROXYALKANOATE (PHAS) USING HALOBACTERIUM AND HALOBACTERIUM

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 2,375 bytes ASCII (Text) file named "706125SequenceListing.txt," created Feb. 17, 2010.

TECHNICAL FIELD

The present invention relates to a method for producing biodegradable plastics, i.e., polyhydroxyalkanoates (PHAs), using a halobacterium, and relates to the halobacterium belonging to the genus *Halomonas*.

BACKGROUND ART

Biodegradable plastics have attracted attention from the standpoint of the prevention of environmental destruction, because they are decomposed by the action of microorganisms and the like in, for example, soil. Compared to general persistent plastics, biodegradable plastics were once more expensive and inferior in performance; however, biodegradable plastics overcame such drawbacks and are now being used in practical application. Demand has increased for mass production technologies for biodegradable plastics along with an increase in the usage of biodegradable plastics.

Polyhydroxyalkanoates, which are a type of biodegradable plastic, are produced by a wide range of bacteria, such as hydrogen bacteria (Ralstonia), cyanobacteria, and methanotrophs, under conditions lacking some kinds of nutrients (nitrogen, phosphorus, etc.).

Meanwhile, halobacteria reportedly accumulate a remarkable amount of PHB in the bacterial cells when grown in a medium with a pH of 7.5 to 8.56 using glucose and the like as the primary carbon source and containing a small amount of peptone and/or yeast extract (for example, see Non-Patent Documents 1 and 2).

Non-Patent Document 1: Quillaguaman J., Munoz M., Mattiasson B., Hatti-Kaul R., "Optimizing conditions for poly (beta-hydroxybutyrate) production by *Halomonas boliviensis* LC1 in batch culture with sucrose as carbon source.", Appl Microbiol Biotechnol. 2007; 74(5): 981-986

Non-Patent Document 2: Quillaguaman J., Hashim S., Bento F., Mattiasson B., Hatti-Kaul R., "Poly(beta-hydroxybutyrate) production by a moderate halophile, *Halomonas boliviensis* LC1 using starch hydrolysate as substrate.", J Appl Microbiol. 2005; 99(1): 151-157

DISCLOSURE OF THE INVENTION

Problems to be Solved by the Invention

An object of the present invention is to provide an inexpensive method for producing PHAs stably even in the event of contamination by other bacteria. Another object of the invention is to provide a PHA-producing halobacterium that does not necessitate the use of a medium containing several organic carbon and nitrogen sources, such as peptone and yeast extract, for their growth, and that can grow under high salt concentration and high alkalinity conditions.

Means for Solving the Problems

The present inventors examined an efficient method of culturing *Spirulina* microalgae, which is known to have little contamination during commercial outdoor incubation, and found that halobacteria grew under certain conditions as only contaminating bacteria.

Since the halobacteria grew well in an alkaline medium (pH 8.8 or higher) containing a high concentration of sodium, it was presumed that contamination by other bacteria hardly occurred. Then, in order to examine the assimilative properties of various carbon sources, the cells of the halobacteria were cultured, and the production of PHAs was examined. The results confirmed a remarkable amount of PHA accumulation.

The various carbon sources used were hexoses (glucose and fructose), pentoses (xylose and arabinose), disaccharide (sucrose), sugar alcohols (mannitol and sorbitol), acetic acid, sodium acetate, ethanol, glycerol, soluble starch, n-propanol, propionic acid, and the like.

In the known documents, every medium used to culture halobacteria contains peptone and yeast extract, suggesting that the use of a small amount of these organic carbon and nitrogen sources, in addition to the primary carbon source, enhances the accumulation of PHAs (Non-Patent Documents 1 and 2).

However, the present inventors confirmed that without using peptone and yeast extract, the halobacteria can be cultured in an inexpensive medium containing an inorganic salt and a simple organic carbon source. Accordingly, the method of the present invention and the halobacteria can be said to be advantageous to actual commercial incubation.

The present inventors found that a certain halobacterium performed the growth process and the PHA accumulation process while converting both processes automatically and continuously, and accumulated a remarkable amount of PHAs using a single organic carbon source as a substrate, even without supplying several types of expensive organic carbon and nitrogen sources including peptone, yeast extract, etc. The present invention was accomplished upon further studies based on these findings, and provides the following PHA production method and halobacterium.

Item 1. A method for producing polyhydroxyalkanoates (PHAs) using a halobacterium belonging to the genus *Halomonas*, wherein the halobacterium can grow in a medium consisting of an inorganic salt and a single organic carbon source and having a pH of 8.8 to 11, and produce PHAs in an amount of 20 wt. % or more based on the dry cell weight; and the halobacterium is cultured in an alkaline medium containing an inorganic salt and one or more organic carbon sources to produce PHAs in an amount of 20 wt. % or more based on the dry cell weight.

Item 2. The method according to Item 1, wherein the concentration of the inorganic salt is 0.2 to 1.0 M.

Item 3. The method according to Item 1 or 2, wherein the polyhydroxyalkanoates contain polyhydroxybutyrate (PHB).

Item 4. The method according to Item 1 or 2, wherein the organic carbon sources include glycerol, and the polyhydroxyalkanoates contain polyhydroxybutyrate.

Item 5. The method according to Item 1 or 2, wherein the organic carbon sources include at least one member selected from the group consisting of n-propanol, propionic acid, and salts thereof, and the polyhydroxyalkanoates contain a copolymer of hydroxybutyrate and hydroxyvalerate (polyhydroxyvalerate: PHV).

Item 6. The method according to any one of Items 1 to 5, wherein the halobacterium is *Halomonas* sp. KM-1 strain (FERM BP-10995).

Item 7. A halobacterium belonging to the genus *Halomonas*, which can grow in a medium consisting of an inorganic salt and a single organic carbon source and having a pH of 8.8 to 11, and produce PHAs in an amount of 20 wt. % or more based on the dry cell weight.

Item 8. The halobacterium according to Item 7, which is *Halomonas* sp. KM-1 strain.

Effect of the Invention

According to the PHA production method of the present invention using a halobacterium, PHAs can be accumulated by one-step incubation in an environment wherein contamination by other bacteria is less likely to occur, without using expensive organic carbon and nitrogen sources, such as peptone and yeast extract, as conventionally used in the production of PHAs. In the present invention, it is not necessary for the growth of the halobacterium to use a medium containing several organic carbon and nitrogen sources, such as peptone and yeast extract; therefore for example, the halobacterium can be used in the treatment of BDF waste containing glycerol etc. and having a high salt concentration, and can be co-cultured with *Spirulina*, which is photosynthetic microalgae, and the like.

Moreover, when sugar etc. are used as a substrate, a homopolymer of hydroxybutyrate is formed; and when n-propanol or propionic acid is used as an organic carbon source for culture, a copolymer containing not only hydroxybutyrate, but also hydroxyvalerate in an amount of up to 13%, as constituent components can be prepared.

In the production of biodiesel fuel (BDF), which is increasingly used as environment-friendly fuel, the mainstream method is to produce fatty acid methyl ester (the main body of BDF) from vegetable and animal fat and oil using alkaline catalysts, such as potassium hydroxide and sodium hydroxide. This technique poses a problem in the treatment of waste glycerol that contains a large amount of alkali. However, after removing methanol, such waste glycerol can be used as a carbon source by the halobacterium to produce PHAs.

Furthermore, the halobacterium will presumably be effective in the production of PHAs during wastewater treatment in which insoluble organic substances are removed by filtration etc. from alkaline waste liquid (pickle waste liquid etc.) that contains a high concentration of salt.

BRIEF DESCRIPTION OF THE DRAWINGS

FIG. 6 is a graph showing the culture time and the culture turbidity $OD_{600}$ when halophilic bacterium *Halomonas* sp. KM-1 strain was cultured using waste glycerol and the like.

BEST MODE FOR CARRYING OUT THE INVENTION

Halobacterium

The present invention provides a halobacterium belonging to the genus *Halomonas*, which can grow in a medium consisting of an inorganic salt and a single organic carbon source and having a pH of 8.8 to 11, and can produce PHAs in an amount of 20 wt. % or more based on the dry cell weight.

The inorganic salt and organic carbon source are the same as those described later.

The halobacterium belonging to the genus *Halomonas* can produce PHAs in an amount of preferably 25 wt. % or more, and more preferably 30 wt. % or more, based on the dry weight of the cells in the medium.

The members of the genus *Halomonas* are halophilic bacteria that favor a salt concentration of about 0.2 M or more but less than 1.0 M, and that may grow in a salt-free medium.

The halobacterium belonging to the genus *Halomonas* favors a salt concentration of about 0.2 M or more but less than 1.0 M. As such a halobacterium belonging to the genus *Halomonas*, *Halomonas* sp. KM-1 strain is preferred, although any halobacteria can be used as long as they can grow in a medium having a pH of 8.8 or more, preferably 8.8 to 11, without using several organic carbon and nitrogen sources such as peptone and yeast extract, and can produce PHAs in an amount of 20 wt. % or more based on the dry weight of the cells in the above medium. The *Halomonas* sp. KM-1 strain is characterized in that it can be cultured in a medium consisting of an inorganic salt and a single organic carbon source and having a pH of 8.8 or more, preferably 8.8 to 11, and can produce PHAs in an amount of 20 wt. % or more based on the dry weight of the cells in the medium.

Further, the *Halomonas* sp. KM-1 strain has a 16S rRNA gene comprising a base sequence represented by SEQ ID NO: 1 in the sequence listing.

The following describes mycological properties of the *Halomonas* sp. KM-1 strain.

A colony cultured in modified SOT medium (explained later) at 37° C. for about 24 hours has a diameter of 1.0 to 1.5 mm and a color tone ranging from very light orange to light beige, which becomes whitish when refrigerated for a long period of time. The form of the colony is circular; the raised state is semilenticular; the edge is wavy; and the surface is smooth, opaque and viscous.

The color of the colony, which is light orange to light beige at the beginning of growth, becomes whitish after a few days. It is difficult to form a fine single colony; in the case of streak culture, continuous colonies are easily formed.

The sterilization conditions for the medium are as follows: autoclave at 121° C. for 15 minutes, or filter sterilization (0.2 μm); in normal incubation, aerobic culture at 20 to 37° C., and culture period for 12 to 24 hours. Light is not necessary for the growth. The halobacterium can be stored by freeze-drying in which 10% of skim milk and 1% of sodium glutamate are used as protective agents and the storage temperature is 5° C. The recovery after freeze-drying is carried out in modified SOT medium that contains 1% of sodium acetate as a carbon source.

The halobacterium can also be stored by freezing at around −80° C. using a 30% glycerol solution.

According to 16S ribosomal RNA sequence analysis, the *Halomonas* sp. KM-1 strain is particularly highly homologous to *Halomonas nitrophilus* of the genus *Halomonas*, and also homologous to *Halomonas daqingensis, Halomonas salina, Halomonas alimentaria, Halomonas campisalis, Halomonas desiderata*, and the like.

The *Halomonas* sp. KM-1 strain was deposited with the National Institute of Advanced Industrial Science and Technology International Patent Organism Depositary (Tsukaba Central 6, 1-1-1 Higashi, Tsukaba-shi, Japan) under the accession number FERM P-21316 on Jul. 10, 2007, and has been internationally deposited under the accession number FERM BP-10995.

The present inventors separated the *Halomonas* sp. KM-1 strain from a medium of *Spirulina* strain. The observation of the association between the culture of *Halomonas* sp. KM-1 strain and the PHA production revealed that although a very small amount of PHAs was produced during the induction culture phase, when the cell density became high ($OD_{600}$=2.0 or more) in the second half of the logarithmic growth phase, PHAs were accumulated in the bacterial cells in an amount as much as 20 wt. % or more per dry cell, several hours after the growth of the bacterial cells. Since these processes are performed in a series of bacterial cell growth, no special changes are necessary for the operation (refer to Examples, and FIGS. 1 and 2). The *Halomonas* sp. KM-1 strain can contain PHAs in an amount of 20 wt. % or more per dry cell, and 40 to 95 wt. % per dry cell depending on the conditions.

As a result of 16S ribosomal RNA sequence analysis, specific examples of the halobacterium other than the *Halomonas* sp. KM-1 strain include *Halomonas nitrophilus, Halomonas alimentaria*, and the like.

In addition to *Halomonas nitrophilus, Halomonas* sp. KM-1, etc., any halobacteria that belong to the genus *Halomonas* and have the same properties as the above-mentioned bacteria are applicable to the PHA production method of the present invention using a halobacterium, and may be used as the halobacterium of the present invention.

Moreover, it is possible to introduce genes into the halobacterium belonging to the genus *Halomonas*.

The introduction of genes is carried out in the following manner. Recombinant DNA, in which the genes to be introduced can be expressed in a host cell, is produced. The recombinant DNA is introduced into the host cell for transformation. For example, it is preferable to use an expression plasmid obtained by using a plasmid vector replicable in the host bacterium, and locating a promoter, SD (Shine and Dalgarno) base sequence, and initiation codon (e.g., ATG) necessary for the initiation of protein synthesis, upstream of the gene so that the gene can be expressed in this vector. As the method of introducing the desired recombinant DNA obtained in this way to the host cell, and the method of transforming with the recombinant DNA, various general methods are adoptable.

Method of Producing PHAs (a) Medium

In the present invention, the halobacterium is cultured in an alkaline medium containing an inorganic salt and a single or several types of organic carbon sources, and preferably containing an inorganic salt and a single organic carbon source.

Examples of inorganic salts include phosphate, sulfate, and salts of metals such as sodium, magnesium, potassium, manganese, iron, zinc, copper, cobalt, and the like. Components of a sodium-containing medium may be NaCl, $NaNO_3$, $NaHCO_3$, $Na_2CO_3$, etc. Several types of inorganic salts may be used, and the concentration of the inorganic salts is preferably 0.2 to 2.5 M, more preferably 0.2 to 1.0 M, and particularly preferably about 0.2 to 0.5 M, in the total amount.

Examples of organic carbon sources include hexoses (glucose and fructose), pentoses (xylose and arabinose), disaccharide (sucrose), sugar alcohols (mannitol and sorbitol), acetic acid, sodium acetate, ethanol, glycerol, soluble starch, n-propanol, propionic acid, etc; ethanol, n-propanol, propionic acid, glucose, xylose, glycerol, and sucrose are preferred. Such organic carbon sources may be used singly or in combination, and appropriate concentrations vary depending on carbon sources. When using glycerol, for example, the amount of organic carbon sources in the medium is 0.1 to 20 w/v %, and preferably 2 to 10 w/v %.

The medium may partially contain components other than inorganic salts and organic carbon sources. When using waste glycerol, for example, such components include secondary organic carbon sources such as fatty acid and fatty acid ester, metals derived from the catalyst such as potassium and sodium, and the like.

The pH of the medium may be 5 or more, preferably alkaline, and depending on the bacterial species, preferably 8.8 or more, and particularly preferably 8.8 to 11.

Since the halobacterium is cultured in a medium under alkaline conditions and high salt concentrations, contamination by other bacteria hardly occurs. Additionally, since a single inexpensive carbon source is used, culture can be performed at a low cost.

Waste glycerol containing a large amount of alkali is discharged during the production of biodiesel fuel (BDF). Such waste glycerol can be used, after the removal of methanol, as an organic carbon source in the above-described medium. Waste glycerol contains, for example, about 350 to 400 mg/g of glycerol and about 41 to 62 mg/g of potassium. When 1 g of waste glycerol is dissolved in 100 ml of distilled water, the pH is about 10.3 to 10.4. The amount of waste glycerol added to the medium is 1 to 20 wt. %, and preferably 3 to 10 wt. %.

(b) Culture Method

The method of culturing the halobacterium of the present invention is not limited as long as it can produce PHAs. An example of culture is provided below.

The halobacterium belonging to the genus *Halomonas* including the *Halomonas* sp. KM-1 strain are inoculated in an about 5 ml of medium, and pre-cultured with shaking at a stirring rate of 120 to 180 rpm at about 30 to 37° C. overnight.

The pre-cultured cells are diluted about 100 to 1,000 times and cultured in a medium that is placed in an Erlenmeyer flask, fermenter, or the like. The main culture is preferably carried out at 30 to 37° C., although it is possible to carry out the main culture at 20 to 45° C.

Although the time necessary for culture varies depending on the conditions of the medium, the optimal culture time for each medium condition will allow for the production of 20 wt. % or more of PHAs based on the dry cell weight.

(c) PHAs

The PHAs produced according to the present invention are polymers comprising a hydroxyalkanoate unit, and examples of hydroxyalkanoates include hydroxybutyrate, hydroxyvalerate, and the like. Many of the PHAs are homopolymers comprising the same hydroxybutyrate. Culture using n-propanol, propionic acid, or salts thereof as a carbon source can produce PHA copolymers comprising hydroxybutyrate and hydroxyvalerate. In this case, the hydroxyvalerate content is 0.5 to 13%, and preferably 5 to 13%.

The PHAs accumulated in the bacterial cells can be collected in a standard manner. For example, the cells can be crushed, followed by extraction with trichloroethylene.

The content of the PHAs produced by the present invention is 20 to 95 wt. %, and preferably 50 to 95 wt. %, based on the dry cell. The PHB content is 20 to 95 wt. %, preferably 50 to 80 wt. %, based on the dry cell.

The PHAs produced from the *Halomonas* sp. KM-1 strain have a number average molecular weight (MN) of about 400,000 and a weight average molecular weight (MW) of about 560,000. Hence, the PHAs can sufficiently be used for general application. PHAs having similar values of MN and MW can also be obtained from other halobacteria belonging to the genus *Halomonas*.

EXAMPLES

The present invention is described in detail below with reference to Examples.

The Examples illustrate a method of producing polyhydroxyalkanoates (PHAs), which are biodegradable aliphatic-polyester plastics produced by microorganisms.

Medium Composition

The media used were SOT media (available from the National Institute for Environmental Studies) to which each carbon source had been added.

Medium name: modified SOT (modified *Spirulina platensis* medium)

Medium constituents:

| | | | |
|---|---|---|---|
| $NaHCO_3$ | 1.68 g | $K_2HPO_4$ | 50 mg |
| $NaNO_3$ | 250 mg | $K_2SO_4$ | 100 mg |
| NaCl | 100 mg | $MgSO_4 \cdot 7H_2O$ | 20 mg |
| $CaCl_2 \cdot 2H_2O$ | 4 mg | $FeSO_4 \cdot 7H_2O$ | 1 mg |
| $Na_2$ EDTA | 8 mg | A5 + Co solution | 0.1 ml |

For example, 1.0 g of sodium acetate is used as a carbon source. All of the constituents are dissolved in distilled water, and the total amount is adjusted to 100 ml.

| A5 + Co solution (modified) | | | |
|---|---|---|---|
| $H_3BO_3$ | 286 mg | $MnSO_4 \cdot 7H_2O$ | 250 mg |
| $ZnSO_4 \cdot 7H_2O$ | 22.2 mg | $CuSO_4 \cdot 5H_2O$ | 7.9 mg |
| $Na_2MoO_4 \cdot 2H_2O$ | 2.1 mg | $Co(NO_3)6H_2O$ | 4.398 mg |
| Distilled water | 100 ml | | |

In sterilization, the above medium constituents are divided into two groups:

SOT-A: ($NaHCO_3$: 1.68 g, $K_2HPO_4$: 50 mg/50 ml) double-concentrated aqueous solution SOT-B: (the constituents other than the above: 50 ml) double-concentrated aqueous solution (in the case of plate culture, agar at a final concentration of 1.5 w/v % is added to SOT-B)

Each solution is independently sterilized by autoclave. After cooling to 50° C. or lower, both solutions are mixed. The pHs in liquid culture and plate culture after adjusting the medium are both 8.9±0.1.

Selection of PHA-Producing Bacterium

Bacteria were inoculated on a plate containing various single carbon sources and 0.5 μg/ml of Nile red and screened. They were cultured at 30° C. for two days. The generated colonies were made fluorescent under ultraviolet light of 365 nm, thereby selecting *Halomonas* sp. KM-1 strain that produced PHAs (based on the qualitative PHB production analysis of the following document). According to this method, a strain containing several percent or more of PHAs can qualitatively be selected. Patricia Spiekermann, Bernd H. A. Rehm, Rainer Kalscheuer, Dirk Baumeister, A. Steinbüchel, "A sensitive, viable-colony staining method using Nile red for direct screening of bacteria that accumulate polyhydroxyalkanoic acids and other lipid storage compounds", Archives of Microbiology. 1999; 171(2): 73-80

Analysis Result of 16S Ribosomal RNA Sequence of PHA-Producing Bacterium *Halomonas* sp. KM-1 Strain The 16S ribosomal RNA of the selected PHA-producing bacterium *Halomonas* sp. KM-1 strain was amplified by the PCR method and purified. Using this as a template, the sequence was analyzed. The sequence is shown in SEQ ID NO: 1 of the sequence listing, and is 1,535 bp long.

Pre-Culture of PHA-Producing Bacterium *Halomonas* sp. KM-1 Strain

After plate culture, 5 ml of each of the above media (containing 1 w/v % of a carbon source) was placed in a 16.5-mm diameter test tube, and culture with shaking at 37° C. was carried out overnight.

Culture of PHA-Producing Bacterium *Halomonas* sp. KM-1 Strain, Collection of Samples, etc.

The pre-cultured bacterial cells (0.1 ml) were inoculated in 30 ml of liquid medium that was put in a 100-ml Erlenmeyer flask, and the flask was closed with Silicosen. Culture with shaking at 30° C. was carried out. After 12 hours, 1 ml of culture medium was collected at intervals of about 12 hours, and the $OD_{600}$, dry cell weight, and PHA content were measured. After again closing the flask with Silicosen, culture with shaking at 30° C. was continued.

The bacterial cell turbidity $OD_{600}$, the ratio of PHAs per dry cell weight, the ratio of PHB per dry cell weight, and the ratios of hydroxybutyrate and hydroxyvalerate per dry cell weight when using n-propanol or propionic acid as a substrate were each relativized with respect to the culture time, and plotted in FIGS. 1, 2, 3 and 4.

Figure 2:
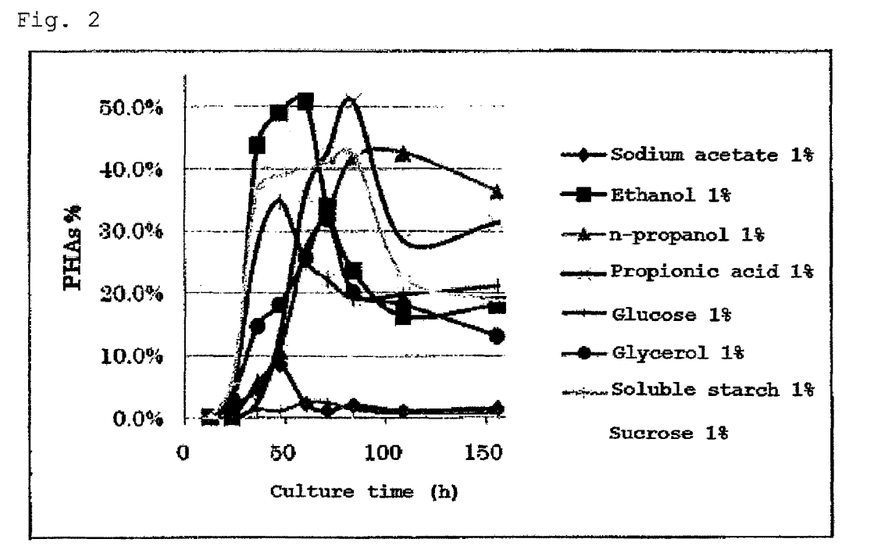
FIG. 2 is a graph showing the ratio of accumulated PHAs (PHAs/dry cell) and the culture time when halophilic bacterium *Halomonas* sp. KM-1 strain was cultured using various carbon sources.

The values of the ratio of PHAs per dry cell weight (%) in FIG. 2 are shown in the following table.

TABLE 1

| | | Culture time (h) | | | | | | | |
|---|---|---|---|---|---|---|---|---|---|
| | | 12.0 | 23.0 | 36.0 | 47.0 | 60.0 | 71.0 | 84.0 | 109.0 | 156.0 |
| Carbon source | Sodium acetate 1% | 0% | 1.6% | 4.4% | 8.4% | 2.2% | 1.0% | 1.9% | 1.0% | 1.4% |
| | Ethanol 1% | 0% | 0% | 43.7% | 49.0% | 50.8% | 33.8% | 23.5% | 16.1% | 18.0% |
| | N-propanol 1% | 0% | 0% | 5.6% | 10.6% | 26.8% | 32.8% | 41.8% | 42.6% | 36.3% |
| | Propionic acid 1% | 0% | 0% | 2.2% | 12.6% | 35.8% | 42.5% | 50.7% | 28.3% | 31.3% |
| | Glucose 1% | 0% | 4.1% | 27.6% | 34.7% | 25.0% | 22.1% | 19.0% | 19.6% | 21.0% |
| | Glycerol 1% | 0% | 2.9% | 14.6% | 18.0% | 25.5% | 31.9% | 20.0% | 18.0% | 13.0% |
| | Soluble starch 1% | 0% | 0% | 1.2% | 1.0% | 2.3% | 2.4% | 1.3% | 0.7% | 0.7% |
| | Sucrose 1% | 0% | 5.3% | 36.7% | 38.6% | 40.0% | 41.0% | 42.6% | 22.7% | 18.8% |

Figure 1:
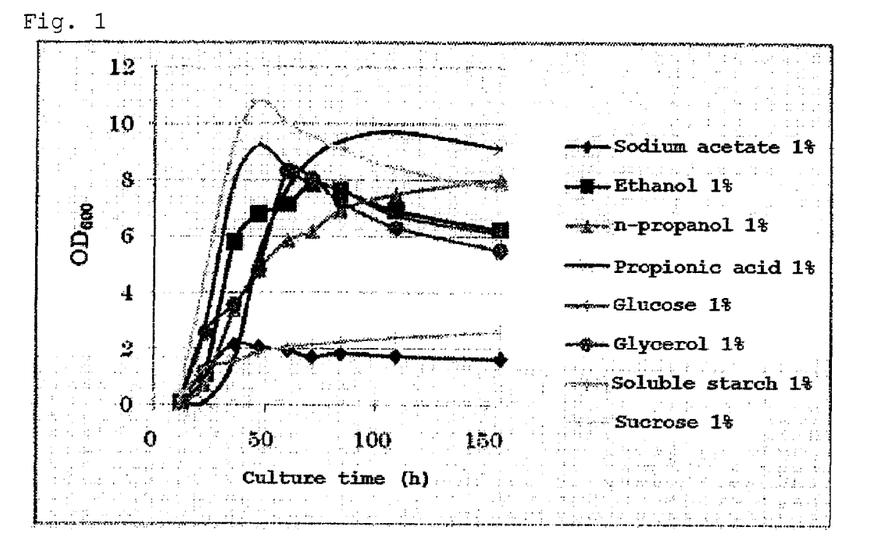
FIG. 1 is a graph showing the culture turbidity $OD_{600}$ and the culture time when halophilic bacterium *Halomonas* sp. KM-1 strain was cultured using various carbon sources. The term "%" shown in the legend represents "w/v %" (the same applies to FIGS. 2 to 5).

Referring to FIG. 1, sucrose, glucose, and sodium acetate show the highest cell density ($OD_{600}$) in about 50 hours; ethanol and glycerol in about 60 to 70 hours; and N-propanol, propionic acid, and soluble starch after 100 hours.

In view of FIG. 2, the amount of PHAs increases with the increase in cell density after a delay of about 10 hours. The amount of PHAs per dry cell declined after reaching the maximum level.

Figure 3:
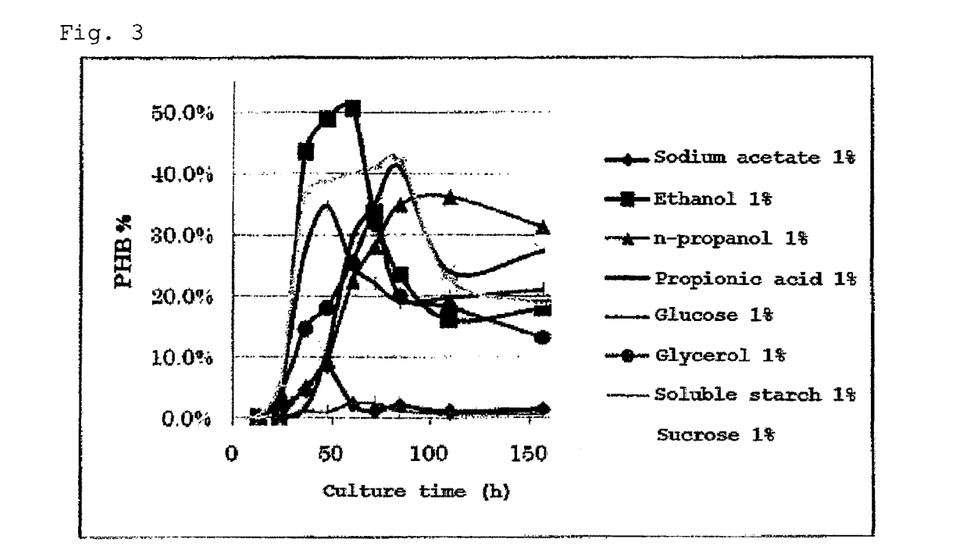
FIG. 3 is a graph showing the ratio of accumulated PHB (PHAs/dry cell) and the culture time when halophilic bacterium *Halomonas* sp. KM-1 strain was cultured using various carbon sources.

FIG. 3 shows the amount of PHB alone per dry cell. The results are the same as in the graph of PHAs in FIG. 2, except for the results of n-propanol and propionic acid.

Figure 4:
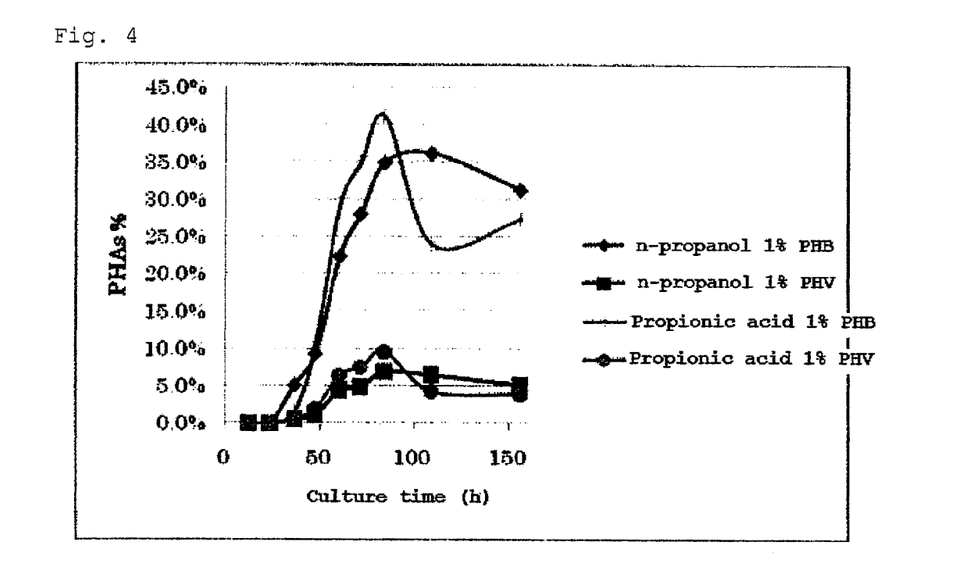
FIG. 4 is a graph showing the ratios of accumulated PHB and PHV (PHAs/dry cell) and the culture time when halophilic bacterium *Halomonas* sp. KM-1 strain was cultured using n-propanol or propionic acid.

FIG. 4 shows the amounts of accumulated hydroxybutyrate and hydroxyvalerate when using n-propanol or propionic acid as a substrate. In the early stages of accumulation, the ratio of hydroxyvalerate is slightly higher. The results suggested the possibility of the production of copolymers having different properties depending on the growth period.

Measurement of Rate of PHA Accumulation

In order to measure the amount of PHAs accumulated in the cells, the following experiment was conducted using the technique described in the document below.

Fanny Monteil-Riveraa, Aimesther Betancourta, Huu Van Trab, Abdessalem Yezzaa, Jalal Hawaria, "Use of headspace solid-phase microextraction for the quantification of poly(3-hydroxybutyrate) in microbial cells", Journal of Chromatography A. 2007; 1154(1-2): 34-41

The above cultured medium was centrifuged to obtain the bacterial cells alone, and the cells were washed with distilled water several times and then dried. Methanol (0.2 ml) containing 3 vol. % $H_2SO_4$ was added to 1 to 3 mg of the dry cells, and heated at 105° C. for 2 hours. After the mixture was cooled to room temperature, 0.2 ml of chloroform and 0.1 ml of distilled water were added and vigorously stirred. After centrifugation for one minute, 2 μl of chloroform layer was taken, and PHAs were analyzed using a gas chromatography apparatus. A preparation containing hydroxybutyrate and hydroxyvalerate was treated and analyzed in the same manner as for the dry cells. Based on the preparation, the PHA accumulation rate per dry cell (PHAs (g)/dry cell weight (g)) was calculated.

Average Molecular Weight of PHAs

In order to measure the average molecular weight of PHAs accumulated in the bacterial cells of the *Halomonas* sp. KM-1 strain, the following experiment was conducted.

A medium containing glycerol (1 w/v %) was used for culture and centrifuged. Removing the supernatant, the cells were suspended in distilled water and centrifuged again. The supernatant was removed to leave the cells alone, and the cells were dried. Chloroform (0.5 ml) was added to 5 mg of the dry cells, and heated at 70° C. for 2 hours to dissolve PHAs. After centrifugation, the supernatant was filtered, and the average molecular weight was measured using gel permeation chromatography (hereinafter referred to as GPC).

As for the molecular weight of PHAs accumulated in the cells, the sample containing 50.0% of PHB per dry cell weight had 400,000 (MN) and 560,000 (MW), and the average molecular weight of PHB accumulated in the cells was about 4 to $5.6 \times 10^5$.

Accordingly, it was revealed that high-molecular weight PHAs could be obtained even when the processes starting from the initiation of cell growth to the accumulation of the desired amount of PHAs were continuously carried out.

Example 2

Culture of *Halomonas* sp. KM-1 Strain in Different pH Environments

The halophilic-bacterium *Halomonas* sp. KM-1 strain was cultured in different pH environments using glycerol 3 w/v % as a carbon source, and the PHB ratio (PHAs/dry cell) accumulated in the cells was measured. To the SOT-A ($NaHCO_3$: 1.68 g (0.2 M), $K_2HPO_4$: 50 mg/50 ml) double-concentrated aqueous solution, which was a buffer component, a SOT-A' ($Na_2CO_3$: 2.12 g, $K_2HPO_4$: 50 mg/50 ml) double-concentrated aqueous solution was added, and solutions at pH 10 and pH 10.5 were prepared using a pH meter. Each solution was mixed with the same amount of SOT-B double-concentrated solution, and used as a medium. The PHB ratio of each medium was relativized with respect to the culture time, and plotted in FIG. 5.

Figure 5:
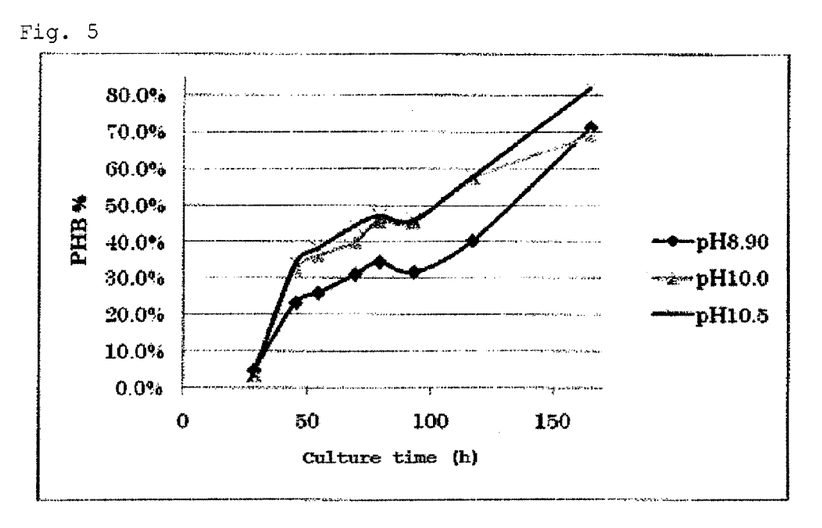
FIG. 5 is a graph showing the ratio of accumulated PHB (PHAs/dry cell) and the culture time when halophilic bacterium *Halomonas* sp. KM-1 strain was cultured in different pH environments using 3 w/v % glycerol as a carbon source.

The *Halomonas* sp. KM-1 strain showed a PHA accumulation rate equal to or more than that at pH 8.9 not only under the normal culture conditions (pH 8.9), but also at pHs 10 and 10.5. Further, the possibility of the utilization of 3 w/v % glycerol was suggested.

Example 3

Table 2 shows the typical compositions of waste glycerol formed as a by-product in the production of biodiesel, which has great potential as an organic carbon source.

TABLE 2

Analysis results of waste glycerol

| | pH | Glycerol (mg/g) | K (mg/g) |
|---|---|---|---|
| Waste glycerol #1 | 10.30 | 350 | 41.8 |
| Waste glycerol #2 | 10.38 | 400 | 62.1 |

TABLE 2-continued

Analysis results of waste glycerol

|  | pH | Glycerol (mg/g) | K (mg/g) |
|---|---|---|---|
| Waste glycerol #3 | 10.35 | 358 | 45.9 |
| Waste glycerol #4 | 10.37 | 358 | 46.0 |

* pH: those measured in samples prepared by dissolving 1 g of waste glycerol in distilled water (total amount: 100 ml) (adapted from Journal of Environmental Conservation Engineering, Vol. 37, No. 5, pp. 48-53)

In general biodiesel production equipment, KOH having a high solubility in methanol is used as an alkaline catalyst.

The waste glycerol actually used for culture was a waste glycerol sample that was kindly provided by the Kyoto Municipal Waste Edible Oil Fuel Production Facility on May 1, 2008.

The pH of this sample was measured in the same manner as described above, and the result was 10.38.

Then, media comprising the medium constituents used above, except for 16.8 g/l of $NaHCO_3$ (buffer component), were prepared. Adding waste glycerol to each media, the *Halomonas* sp. KM-1 strain was cultured. As a control, 5 wt. % of purified glycerol was added to a medium containing $NaHCO_3$. The culture method etc. were the same as described above.

Figure 6:
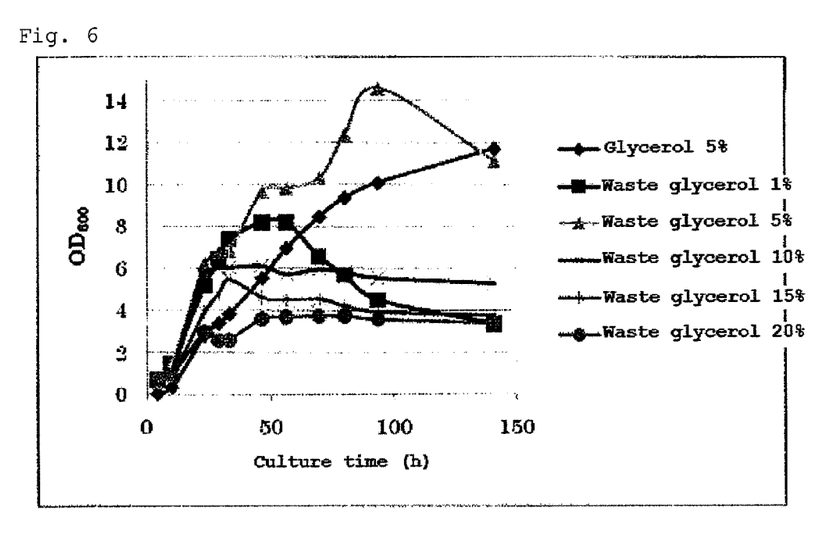

FIG. 6 shows the results. The strain grew in the media containing waste glycerol up to 1 to 20 wt. %, and the growth was better in the medium containing 5 wt. % of waste glycerol than in the medium containing purified glycerol.

Example 4

As medium constituents, the buffer components $NaHCO_3$ and $Na_2CO_3$ were added according to the following formulations at a final concentration of 0.2 M, and the other constituents used were the same as those in the modified SOT, thus preparing media. Adding 1 wt. % of waste glycerol, the growth of the *Halomonas* sp. KM-1 strain was observed. The culture method etc. were the same as described above.

TABLE 3

| | Medium pH | | | |
|---|---|---|---|---|
| | pH 8.90 (same as modified SOT) | Modified SOT 2 pH 9.40 | pH 9.85 | pH 10.28 |
| $NaHCO_3$ | 16.8 g/l | 12.6 g/l | 8.4 g/l | 4.2 g/l |
| $Na_2CO_3$ | 0 g/l | 5.3 g/l | 10.6 g/l | 15.9 g/l |

Figure 7:
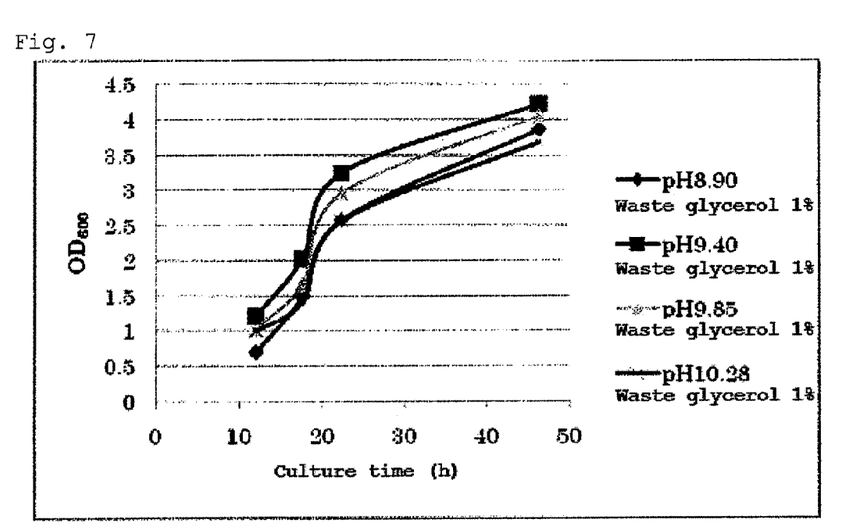
FIG. 7 is a graph showing the culture time and the culture turbidity $OD_{600}$ when halophilic bacterium *Halomonas* sp. KM-1 strain was cultured using waste glycerol etc. $NaHCO_3$ and $Na_2CO_3$ were added to the medium at a final concentration of 0.2 M, and the pH during the growth period was kept constant.

FIG. 7 shows the results. The strain grew at any pH, and the growth was best at pH 9.40. Moreover, the pH after growth was almost equivalent to the initial pH.

Example 5

Using the above modified SOT 2 (pH 9.40) as the medium composition, the *Halomonas* sp. KM-1 strain was cultured under conditions where the concentration of waste glycerol was 3 wt. %, 5 wt. %, or 10 wt. %, and the temperature of the main culture was 30° C. or 37° C. Then, the growth of the strain and the amount of accumulated PHB were observed.

Figure 8:
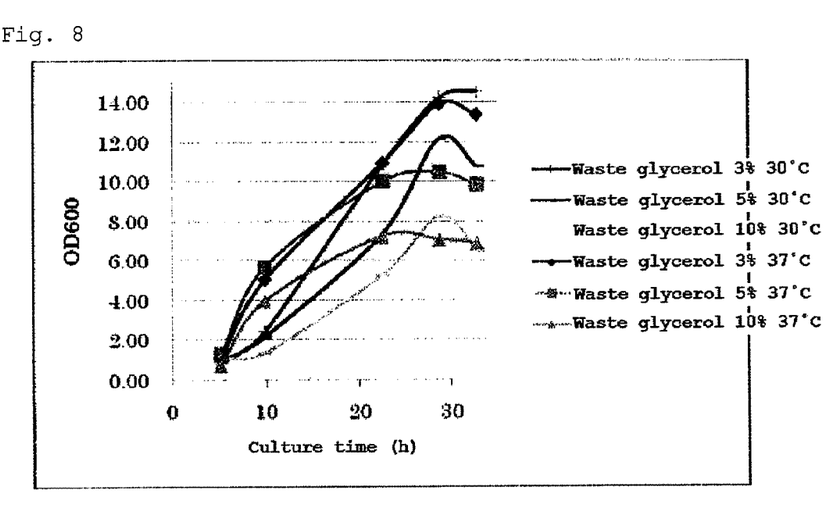
FIG. 8 is a graph showing the culture time and the culture turbidity $OD_{600}$ when halophilic bacterium *Halomonas* sp. KM-1 strain was cultured using waste glycerol. The medium used for growth was modified SOT 2 (pH 9.40).
Figure 9:
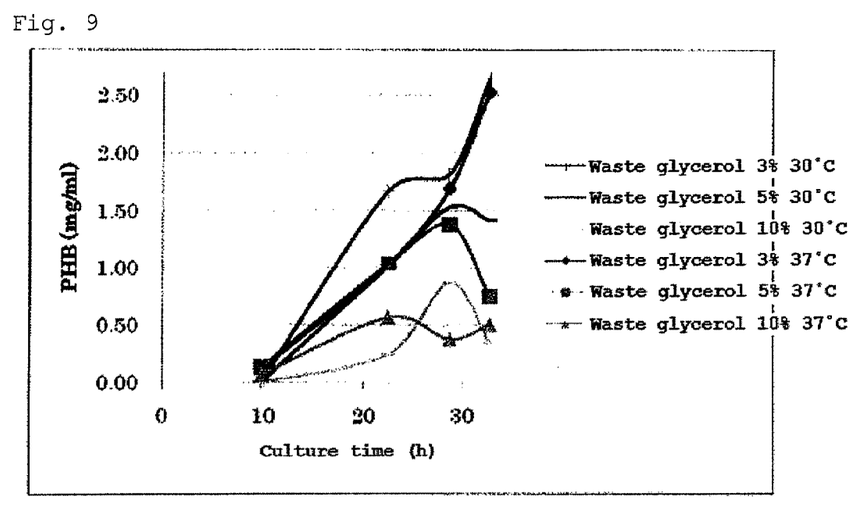
FIG. 9 is a graph showing the culture time and the amount of accumulated PHB per culture medium when halophilic bacterium *Halomonas* sp. KM-1 strain was cultured using waste glycerol. The medium used for growth was modified SOT 2 (pH 9.40).

FIGS. 8 and 9 show the results. The growth was better at 37° C. than at 30° C., while the amount of accumulated PHB was almost the same at both temperatures. When using 3 wt. % of waste glycerol, about 2.5 mg/ml of PHB was accumulated in a culture time of 33 hours at both temperatures.

Example 6

Using the above modified SOT 2 (pH 9.40) as the medium composition, the *Halomonas* sp. KM-1 strain was cultured under conditions where the total concentration of glucose and xylose was 2 w/v %, and the temperature of the main culture was 37° C. Then, the growth of the strain and the amount of accumulated PHB were observed.

Figure 10:
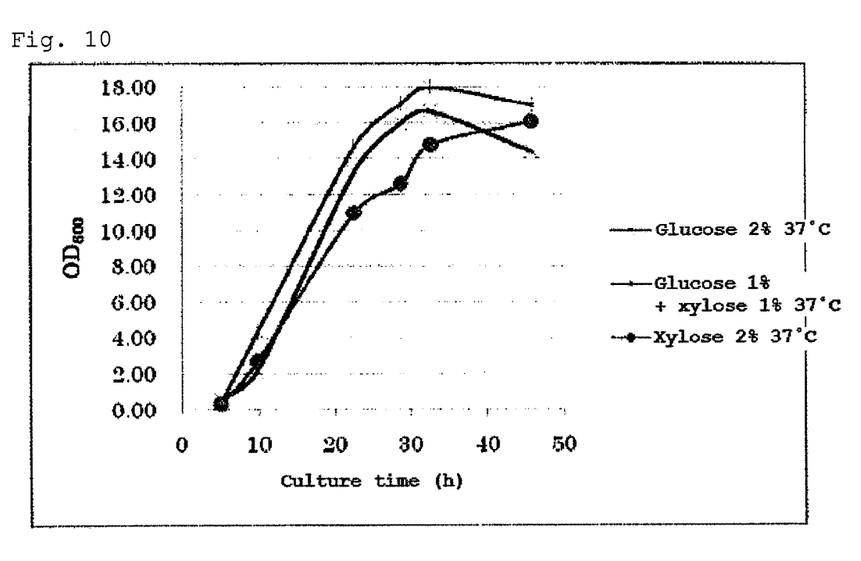
FIG. 10 is a graph showing the culture time and the culture turbidity $OD_{600}$ when halophilic bacterium *Halomonas* sp. KM-1 strain was cultured using glucose and xylose. The medium used for growth was modified SOT 2 (pH 9.40).
Figure 11:
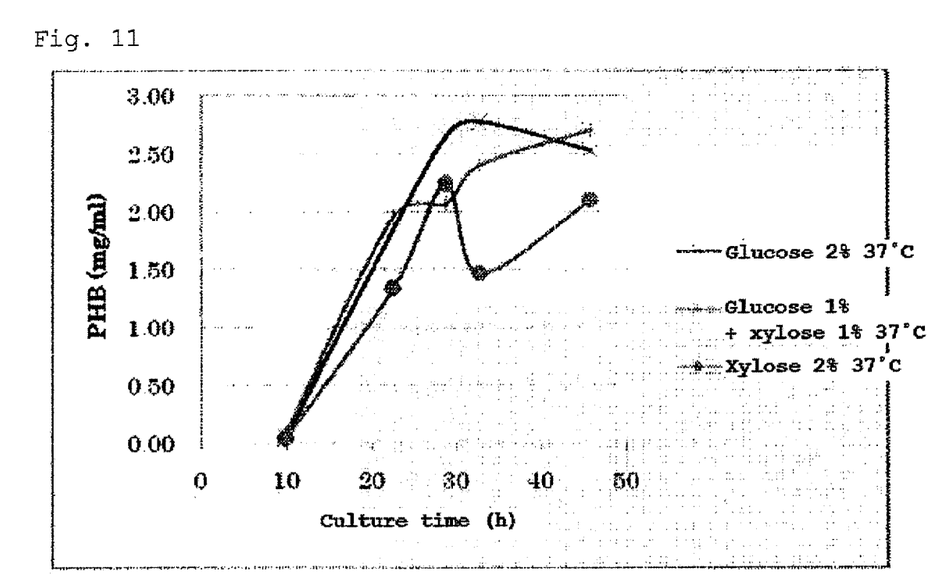
FIG. 11 is a graph showing the culture time and the amount of accumulated PHB per culture medium when halophilic bacterium *Halomonas* sp. KM-1 strain was cultured using glucose and xylose. The medium used for growth was modified SOT 2 (pH 9.40).

FIGS. 10 and 11 show the results. The growth was better when mixing glucose and xylose. The amount of accumulated PHB was not so different when comparing using glucose alone or using a mixture of glucose and xylose. The maximum amount of accumulated PHB was about 2.8 mg/ml based on the culture medium.

Industrial Applicability

The PHA production method of the present invention using a halobacterium is applicable to the industrial production of PHAs.

Sequence Listing

The invention claimed is:

1. An isolated halobacterium of the *Halomonas* sp. KM-1 strain that has been deposited under accession number FERM BP-10995.

2. A method for producing polyhydroxyalkanoates (PHAs) comprising culturing an isolated halobacterium of the *Halomonas* sp. KM-1 strain that has been deposited under accession number FERM BP-10995 in an alkaline medium containing an inorganic salt and one or more organic carbon sources to produce PHAs in an amount of 20 wt. % or more based on the dry cell weight.

3. The method according to claim 2, wherein the concentration of the inorganic salt is 0.2 to 1.0 M.

4. The method according to claim 2, wherein the polyhydroxyalkanoates contain polyhydroxybutyrate (PHB).

5. The method according to claim 2, wherein the organic carbon sources include glycerol, and the polyhydroxyalkanoates contain polyhydroxybutyrate.

6. The method according to claim 2, wherein the organic carbon sources include at least one member selected from the group consisting of n-propanol, propionic acid, and salts thereof, and the polyhydroxyalkanoates contain a copolymer of hydroxybutyrate and hydroxyvalerate (polyhydroxyvalerate: PHV).

* * * * *

```
SEQUENCE LISTING

<160> NUMBER OF SEQ ID NOS: 1

<210> SEQ ID NO 1
<211> LENGTH: 1535
<212> TYPE: DNA
<213> ORGANISM: Halomonas sp. KM-1

<400> SEQUENCE: 1
tggagagttt gatcctggct cagattgaac gctggcggca ggcctaacac atgcaagtcg      60
agcggcagca cgggaagctt gcttcctggt ggcgagcggc ggacgggtga gtaatgcata     120
ggaatctgcc cgatagtggg ggataacctg gggaaaccca ggctaatacc gcatacgccc     180
tacgggggaa agcagggct cttcggacct tgcgctatcg gatgagccta tgtcggatta     240
gctggttggt gaggtaatgg ctcaccaagg cgacgatccg tagctggtct gagaggatga     300
tcagccacat cgggactgag acacggcccg aactcctacg ggaggcagca gtggggaata     360
```

```
ttggacaatg ggcgcaagcc tgatccagcc atgccgcgtg tgtgaagaag gccctcgggt      420
tgtaaagcac tttcagtggg gaagaaagcc tggtggttaa tacccgtcag gaaggacatc      480
acccacagaa gaagcaccgc ctaactccgt gccagcagcc gcggtatacc ggagggtgcg      540
agcgttaatc ggaattactg ggcgtaaagc gcgcgctagg tggcttgata agccggttgt      600
aaagccccgg gctcaacctg ggaacggcat ccggaactgt caggctagag tgcaggagag      660
gaaggtagaa ttcccggtgt accggtaaat gcgtagagat cgggaggaat accagtggcg      720
aaggcggcct tctggacttg acactgacac tgaggtgcga aagcgtgggt agcaaaccag      780
gattagatac cctggtagtc cacgccgtaa acgatgtcga ctagccgttg ggtccttcgc      840
ggactttgtg gcgcagttaa cgcgataagt cgaccgcctg ggagtacggc cgcaaggtta      900
aaactcaaat gaattgacgg ggcccgcaca agcggtggag catgtggttt aattcgatgc      960
aacgcgaaga accttaccta cccttgacat cctgcgaacc cttcggagac gaagggggtgc     1020 cttcgggaac gcagagacag gtgctgcatg gctgtcgtca gctcgtgttg tgaaacgttg     1080
ggttaagtcc cgtaacgagc gcaacccttg tccttatttg ccagcgagta atgtcgggaa     1140
ctctaaggag actgccggtg acaaaccgga ggaaggtggg gacgacgtca agtcatcatg     1200
gcccttacgg gtagggctac acacgtgcta caatggtcgg tacaaagggt tgcgaacttg     1260
cgaaagtgag ctaatcccag aaagctgatc tcagtccgga tcggagtctg caactcgact     1320
ccgtgaagtc ggaatcgcta gtaatcgtga atcagaatgt cacggtgaat acgttcccgg     1380
gccttgtaca caccgcccgt cacaccatgg gagtggactg caccagaagt ggttagccta     1440
accttcggga gggcgatcac cacggtgtgg ttcatgactg gggtgaagtc gtaacaaggt     1500
agccgtaggg gaacctgcgg ctggatcacc tcctt                                1535
```